(12) United States Patent
Patel et al.

(10) Patent No.: US 9,096,509 B2
(45) Date of Patent: Aug. 4, 2015

(54) PROCESS FOR PRODUCING PHENOL

(71) Applicant: ExxonMobil Chemical Patents Inc., Baytown, TX (US)

(72) Inventors: Bryan A. Patel, Arlington, VA (US); Jihad M. Dakka, Whitehouse Station, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/369,865

(22) PCT Filed: Dec. 3, 2012

(86) PCT No.: PCT/US2012/067560
§ 371 (c)(1),
(2) Date: Jun. 30, 2014

(87) PCT Pub. No.: WO2013/109348
PCT Pub. Date: Jul. 25, 2013

(65) Prior Publication Data
US 2014/0371490 A1    Dec. 18, 2014

Related U.S. Application Data

(60) Provisional application No. 61/587,878, filed on Jan. 18, 2012.

(51) Int. Cl.
| | |
|---|---|
| *C07C 45/53* | (2006.01) |
| *C07C 37/08* | (2006.01) |
| *C07C 2/66* | (2006.01) |
| *C07C 407/00* | (2006.01) |
| *C07C 2/74* | (2006.01) |

(52) U.S. Cl.
CPC ............... *C07C 407/00* (2013.01); *C07C 2/74* (2013.01); *C07C 37/08* (2013.01); *C07C 45/53* (2013.01); *C07C 2101/14* (2013.01); *C07C 2531/02* (2013.01)

(58) Field of Classification Search
CPC ............ C07C 45/53; C07C 37/08; C07C 2/74
USPC .................... 568/354, 798; 585/467
See application file for complete search history.

(56) References Cited

U.S. PATENT DOCUMENTS

| | | | |
|---|---|---|---|
| 6,037,513 A | 3/2000 | Chang et al. | |
| 7,038,089 B2 | 5/2006 | De Frutos Escrig et al. | |

FOREIGN PATENT DOCUMENTS

| | | |
|---|---|---|
| WO | 2011/001244 | 1/2011 |

OTHER PUBLICATIONS

Yasutaka Ishii et al., "A Novel Catalysis of N-Hydroxyphthalimide in the Oxidation of Organic Substrates by Molecular Oxygen", J. Org. Chem. 1995, 60, pp. 3934-3935.

*Primary Examiner* — Sikarl Witherspoon
(74) *Attorney, Agent, or Firm* — Siwen Chen; Stephen A. Baehl

(57) ABSTRACT

In a process for producing phenol, a mixture of cyclohexylbenzene with from 10 to 90 wt % of a solvent is contacted with oxygen in the presence of a catalyst and under conditions effective to oxidize at least a portion of the cyclohexylbenzene to cyclohexylbenzene hydroperoxide. The catalyst comprises a cyclic imide having an imide group of formula (I):

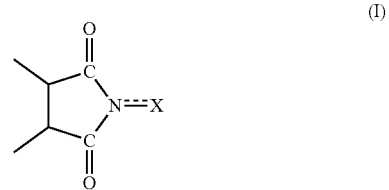

wherein X represents an oxygen atom, a hydroxyl group, or an acyloxy group. At least a portion of the oxygen is dissolved in the mixture and the liquid phase molar ratio of cyclohexylbenzene to oxygen dissolved in the mixture is less than or equal to 20,000:1.

25 Claims, 2 Drawing Sheets

PROCESS FOR PRODUCING PHENOL

PRIORITY CLAIM TO RELATED APPLICATIONS

This application is a National Stage Application of International Application No. PCT/US2012/067560 filed Dec. 3, 2012, which claims priority to U.S. Provisional Application Ser. No. 61/587,878 filed Jan. 18, 2012, the disclosures of which are fully incorporated herein by their reference.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumened. The second step is oxidation, preferably aerobic oxidation, of the cumene to the corresponding cumene hydroperoxide. The third step is the cleavage of the cumene hydroperoxide in the presence of heterogeneous or homogenous catalysts into equimolar amounts of phenol and acetone, a co-product.

It is known that phenol and cyclohexanone can be co-produced by oxidizing cyclohexylbenzene to cyclohexylbenzene hydroperoxide and decomposing the cyclohexylbenzene hydroperoxide in the presence of an acid catalyst to the desired phenol and cyclohexanone. Although various methods are available for the production of cyclohexylbenzene, a preferred route is disclosed in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt, and mixtures thereof. The '513 patent also discloses that the resultant cyclohexylbenzene can be oxidized to the corresponding hydroperoxide which is then decomposed to the desired phenol and cyclohexanone co-product.

There are, however, a number of problems associated with producing phenol via cyclohexylbenzene rather than the cumene-based Hock process. Firstly, oxidation of cyclohexylbenzene to cyclohexylbenzene hydroperoxide is much more difficult than oxidation of cumene and requires elevated temperatures and the use of a catalyst, generally a cyclic imide, such as N-hydroxyphthalimide (NHPI), to achieve acceptable rates of conversion. However, cyclic imide catalysts are expensive and, when used to catalyze the oxidation of cyclohexylbenzene, the selectivity to cyclohexylbenzene hydroperoxide decreases with increasing conversion.

According to the invention, it has now been found that the addition of a controlled amount of a solvent/diluent (e.g., benzonitrile) improves the conversion rate dramatically, even despite the reduced concentration of cyclohexylbenzene in the mixture, while maintaining or increasing the selectivity to cyclohexylbenzene hydroperoxide. In addition, since both NHPI and oxygen have higher solubility in benzonitrile than in cyclohexylbenzene, the addition of benzonitrile allows an increased concentration of oxygen and NHPI in the liquid phase, thereby further improving the conversion rate and the hydroperoxide selectivity.

U.S. Pat. No. 7,038,089 discloses a process for preparing a hydroperoxide from a hydrocarbon selected from a group consisting of primary hydrocarbons, secondary hydrocarbons, and mixtures thereof corresponding to said hydroperoxide which comprises conducting oxidation of said hydrocarbon at a temperature in the range between 130° C. and 160° C. with an oxygen-containing gas in a reaction mixture containing said hydrocarbon and a catalyst comprising a cyclic imide compound and an alkali metal compound. Suitable hydrocarbons are said to include $C_4$ to $C_{20}$ tertiary alkanes (e.g., iso-butane, iso-pentane, iso-hexane, and the like), $C_7$ to $C_{20}$ (alkyl) aromatic hydrocarbons with 1 to 6 aromatic rings or $C_9$ to $C_{20}$ (cycloalkyl) aromatic hydrocarbons with 1 to 6 aromatic rings (e.g., xylene, cumene, cymene, ethylbenzene, diisopropylbenzene, cyclohexylbenzene, tetrahydronaphthalene (tetraline), indane, etc.), and the like. The reaction may be carried out in the presence of a solvent, such as nitriles (e.g., benzonitrile, acetonitrile, etc.), organic acids (e.g., formic acid, acetic acid, etc.), nitro compounds (e.g., nitromethane, nitrobenzene, etc.), chlorohydrocarbons (e.g., chlorobenzene, 1,2-dichloroethane, etc.), and mixtures thereof.

SUMMARY

In one aspect, the invention resides in a process for producing phenol, the process comprising:

(a) providing a mixture comprising cyclohexylbenzene and 10 wt % to 90 wt % of a solvent, the wt % based upon the total weight of the mixture; and (b) contacting the mixture with oxygen in the presence of a catalyst under conditions effective to produce an oxidation effluent comprising cyclohexylbenzene hydroperoxide and residual solvent, wherein the catalyst comprises a cyclic imide having an imide group of formula (I):

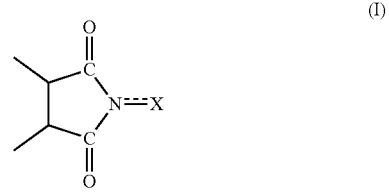

wherein X represents an oxygen atom, a hydroxyl group, or an acyloxy group, and wherein at least a portion of the oxygen is dissolved in the mixture and the liquid phase molar ratio of cyclohexylbenzene to oxygen dissolved in the mixture is less than or equal to 20,000:1.

In a further aspect, the invention resides in a process for producing phenol, the process comprising:

(a) contacting benzene with hydrogen in the presence of a hydroalkylation catalyst and under conditions effective to convert at least a portion of the benzene to cyclohexylbenzene;

(b) mixing at least a portion of the cyclohexylbenzene produced in (a) with a solvent to produce a mixture comprising from 10 wt % to 90 wt % of the solvent, the wt % based upon the total weight of the mixture; and (c) contacting the mixture with an oxygen-containing gas in at least one oxidation zone in the presence of a catalyst and under conditions effective to produce an oxidation effluent comprising cyclohexylbenzene hydroperoxide and residual solvent, wherein the catalyst comprises a cyclic imide having an imide group of formula (I):

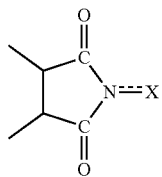

(I)

wherein X represents an oxygen atom, a hydroxyl group, or an acyloxy group, and wherein at least a portion of the oxygen-containing gas is dissolved in the mixture and the liquid phase molar ratio of cyclohexylbenzene to oxygen dissolved in the mixture is less than or equal to 20,000:1.

Conveniently, the molar ratio of cyclohexylbenzene to cyclic imide supplied to said at least one oxidation zone is less than or equal to 10,000:1, typically less than or equal to 2,000:1.

Conveniently, said cyclic imide is of the general formula (II):

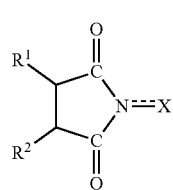

(II)

wherein $R^1$ and $R^2$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^1$ and $R^2$ may be bonded together to form a double bond or an aromatic- or non-aromatic ring.

In one embodiment, said cyclic imide comprises N-hydroxyphthalimide (NHPI).

DETAILED DESCRIPTION OF THE EMBODIMENTS

Figure 1:
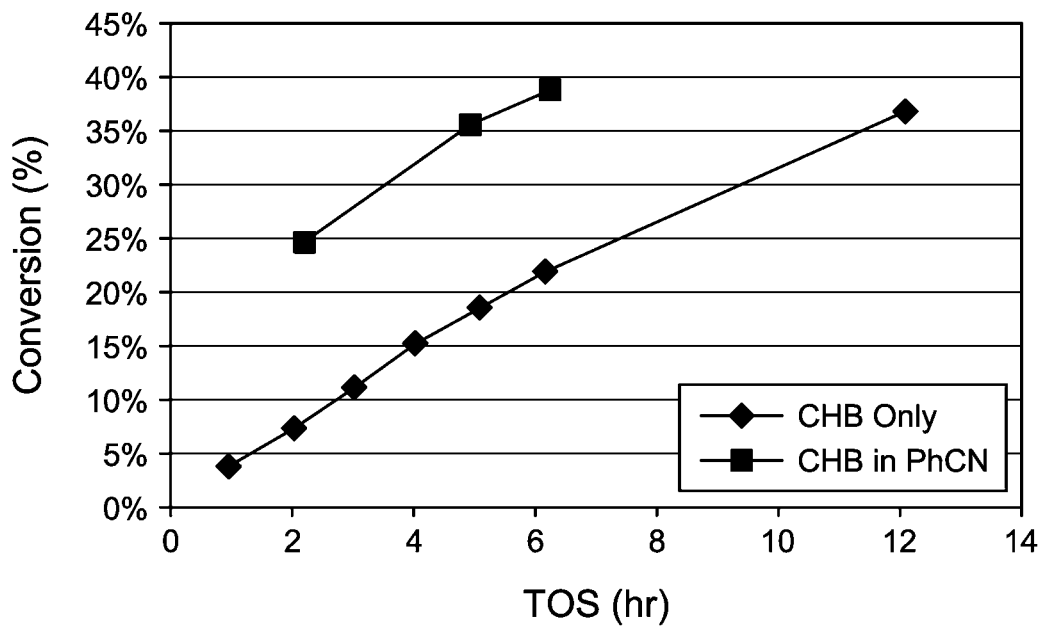
FIG. 1 is a graph comparing cyclohexylbenzene conversion against time on stream at 105° C., 1 atmosphere pressure and 0.2 wt % NHPI for (a) 100% cyclohexylbenzene and (b) a solution of 20 wt % cyclohexylbenzene in benzonitrile (referred to as PhCN).

Described herein is a process for producing phenol by the oxidation of cyclohexylbenzene in a mixture comprising from 10 wt % to 90 wt %, typically 10 wt % to 50 wt %, of benzonitrile, in the presence of a cyclic imide catalyst and at a liquid phase molar ratio of cyclohexylbenzene to dissolved oxygen of less than or equal to 20,000:1. The process is effective in producing cyclohexylbenzene hydroperoxide at a high conversion rate and high selectivity. The resultant cyclohexylbenzene hydroperoxide can then be cleaved in the presence of an acid catalyst to produce phenol and cyclohexanone.

In one preferred embodiment, the present oxidation process forms part of an integrated process for producing phenol and cyclohexanone from benzene, in which the benzene is converted to cyclohexylbenzene, the cyclohexylbenzene is oxidized to cyclohexylbenzene hydroperoxide and the cyclohexylbenzene hydroperoxide is cleaved to produce phenol and cyclohexanone. The present process will therefore now be more particularly described with reference to this preferred embodiment.

Production of the Cyclohexylbenzene

In one step of the integrated process starting from benzene, cyclohexylbenzene is produced by reacting the benzene with cyclohexene in the presence of a catalyst having an alkylation function and under conditions to promote the following reaction:

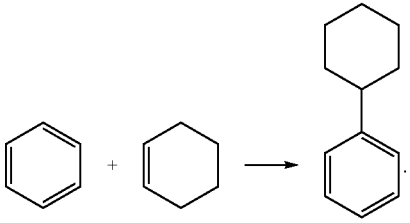 [SMILES: c1ccccc1 ; C1=CCCCC1 ; c1ccc(C2CCCCC2)cc1]

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

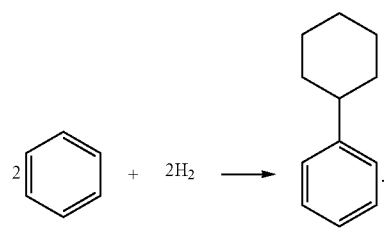 [SMILES: c1ccccc1 ; c1ccc(C2CCCCC2)cc1]

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

- molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);
- molecular sieves made from a common second degree building block, being a 2-dimensional tiling of such MWW framework topology unit cells, forming a monolayer of one unit cell thickness, preferably one c-unit cell thickness;
- molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
- molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene; or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least a portion of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium, and compounds and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 wt % and about 5 wt % of the catalyst. Suitable dehydrogenation conditions include a temperature of about 250° C. to about 500° C., a pressure of about atmospheric to about 14.5 psig to 500 psig (100 kPa to 3550 kPa), a weight hourly space velocity of about 0.2 hr$^{-1}$ to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least a portion of the hydroalkylation reaction product may be treated with a catalyst under conditions to remove at least 1,1-methylcyclopentylbenzene, and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

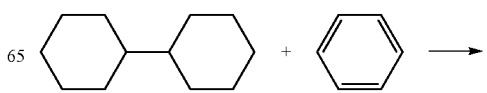

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air, or other conventional means.

The oxidation is conducted in the presence of a catalyst comprising a cyclic imide having an imide group of formula (I):

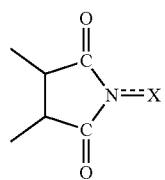

(I)

wherein X represents an oxygen atom, a hydroxyl group, or an acyloxy group.

Generally, the cyclic imide employed as the oxidation catalyst obeys the general formula II:

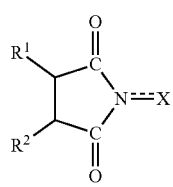

(II)

wherein $R^1$ and $R^2$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^1$ and $R^2$ may be bonded together to form a double bond or an aromatic- or non-aromatic ring.

More specifically, the cyclic imide employed as the oxidation catalyst typically obeys the general formula III:

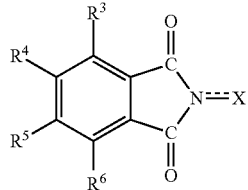

(III)

wherein each of $R^3$, $R^4$, $R^5$, and $R^6$ is independently selected from H, aliphatic or aromatic alkoxy radical, carboxyl radical, alkoxy-carbonyl radical, or hydrocarbon radical, each of which has 1 to 20 carbon atoms, $SO_3H$, $NH_2$, OH, F, Cl, Br, I, and/or $NO_2$.

In one practical embodiment, the cyclic imide catalyst comprises N-hydroxyphthalimide.

The cyclohexylbenzene may be mixed with a solvent (e.g., benzonitrile) prior to or during oxidation in an amount so as to produce a mixture comprising from 10 wt % to 90 wt %, typically 20 wt % to 80 wt %, of the solvent. The cyclohexylbenzene/solvent mixture, the cyclic imide catalyst and the oxygen (e.g., oxygen-containing gas such as air) are supplied to the oxidation reaction in such proportions that the liquid phase molar ratio of cyclohexylbenzene to dissolved oxygen is less than or equal to 20,000:1, typically less than or equal to 2,000:1, for example from 100:1 to 2000:1 and the molar ratio of cyclohexylbenzene to cyclic imide is less than or equal to 10,000:1, typically less than or equal to 2,000:1, for example from 10:1 to 2000:1.

Suitable solvents include polar solvents such as benzonitrile, acetonitrile, sulfolane, carbon disulfide, nitromethane, nitrobenzene, or a mixture of two or more thereof.

In various embodiments, the oxidation reaction produces an oxidation effluent comprising cyclohexylbenzene hydroperoxide and residual solvent. As used herein, "residual solvent" means solvent from the cyclohexylbenzene/solvent mixture that does not react in the oxidation reaction. In various embodiments, at least a portion of the residual solvent is recovered from the oxidation effluent and recycled to the cyclohexylbenzene/solvent mixture prior to or during the oxidation step.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the heat generated in the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent is may be subjected to a cleavage reaction, either directly or after undergoing prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate the imide oxidation catalyst (e.g., NHPI) and other adsorbable compounds, and provide an oxidation composition with a reduced imide content that may be subjected to the cleavage reaction. Similarly, all or a fraction of the oxidation effluent may undergo a chemically or physically based adsorption, such as passage over a bed of sodium carbonate to remove the imide oxidation catalyst and other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939, the entire contents of which is incorporated herein by reference.

In another embodiment, all or a fraction of the oxidation effluent may be contacted with an aluminosilicate zeolite of the FAU type to reduce the amount of unreacted imide catalyst in the effluent by adsorption onto the zeolite. The FAU type zeolite employed to remove the oxidation catalyst may be same as the FAU type zeolite employed in the cleavage reaction, namely having a unit cell size less than 24.50, or less than 24.45, or less than 24.40, or less than 24.35 Å, such as less than 24.30 Å, and the contacting to remove the oxidation catalyst can be conducted prior to or concurrently with the cleavage reaction. The adsorbed imide catalyst can be desorbed from the FAU type zeolite by washing with a polar solvent, such as acetone or cyclohexanone, and recovered by flashing off the solvent and/or by recrystallization. The recovered imide can then be recycled to the oxidation reaction.

Hydroperoxide Cleavage

Another reactive step in the conversion of the cyclohexylbenzene into phenol and cyclohexanone involves the acid-catalyzed cleavage of the cyclohexylbenzene hydroperoxide from the oxidation reaction effluent.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to no greater than 3000 wppm, or at least 150 wppm to no greater than 2000 wppm of the acid catalyst, or at least 300 wppm to no greater than 1500 wppm of the acid catalyst, based upon total weight of the cleavage reaction mixture.

In one embodiment, the cleavage reaction mixture contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

Suitable cleavage conditions include a temperature of at least 20° C. and no greater than 200° C., or at least 40° C. and no greater than 120° C., and a pressure of at least 1 psig and no greater than 370 psig (at least 7 kPa and no greater than 2,550 kPa, gauge), or at least 14.5 psig and no greater than 145 psig (at least 100 kPa and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction are phenol and cyclohexanone, each of which generally comprise about 40 wt % to about 60 wt %, or about 45 wt % to about 55 wt % of the cleavage reaction product, such wt % based on the weight of the cleavage reaction product exclusive of unreacted cyclohexylbenzene and acid catalyst.

The cleavage reaction product also typically contains unreacted acid catalyst and hence at least a portion of the cleavage reaction product is normally neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide, and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay such as limestone, dolomite, magnesite, sepiolite, and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium, and radium; an oxide of Group III of the Periodic Table of Elements treated with a metal selected from lithium, potassium, sodium, rubidium and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines, and alkanolamines. In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on at least a portion of the treated cleavage reaction product that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 psig to about 500 psig (5 kPa to 3450 kPa, gauge), or about 10 psig to 200 psig (70 kPa to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which can be purified and separated by methods well known in the art.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the following non-limiting examples and the accompanying drawings.

Example 1

Oxidation of Cyclohexylbenzene (CHB) using N-Hydroxyphthalimide (NHPI) as Catalyst 150 g of cyclohexylbenzene from TCI America and 0.16 g NHPI from TCI were weighed into a Parr reactor fitted with a stirrer, thermocouple, gas inlet, sampling port, and a condenser containing a Dean-Stark trap for water removal. The reactor contents were stirred at 1000 rpm and sparged with nitrogen at a flow rate of 250 cc/minute for 5 minutes. The reactor was maintained under a nitrogen sparge and heated to 105° C. When the reaction temperature was reached, the gas was switched from nitrogen to air and the reactor was sparged with air at 250 cm³(cc)/minute for 12 hours. Samples were taken periodically and analyzed by gas chromatography. After 12 hours, the gas was switched back to nitrogen and the heat was turned off. The conversion profile is shown in FIG. 1.

Example 2

Oxidation of 20 wt % CHB/80 wt % Benzonitrile using NHPI as Catalyst

The process of Example 1 was repeated but with the cyclohexylbenzene being replaced by 150 g of 20 wt % solution of cyclohexylbenzene in benzontrile (i.e., 30 g of CHB in 120 g of Benzonitrile). The conversion profile is shown in FIG. 1 (PhCN), from which it can be seen that the rate of conversion of was significantly increased by using 20 wt % CHB solution as compared with the CHB alone.

Example 3

Figure 2:
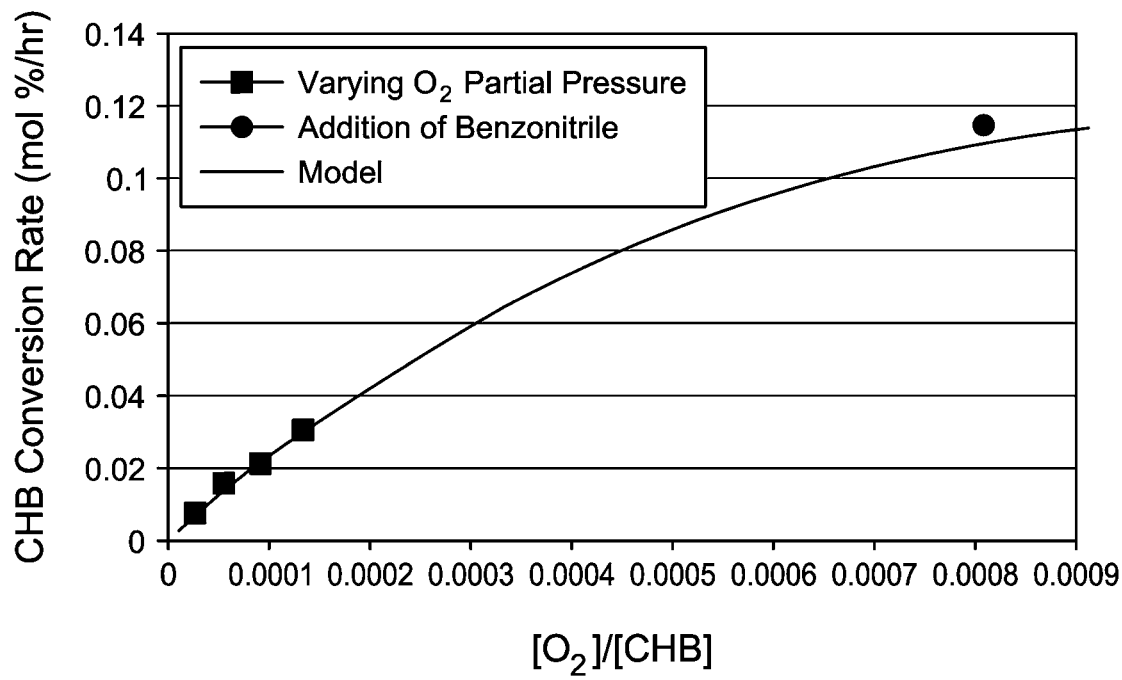
FIG. 2 is a graph of cyclohexylbenzene conversion rate (mole %/hour) against oxygen to cyclohexylbenzene molar ratio at 105° C., 1 atmosphere pressure (100 kPa), and 0.2 wt % NHPI for (a) 100% cyclohexylbenzene and (b) a solution of 20 wt % cyclohexylbenzene in benzonitrile.
Figure 3:
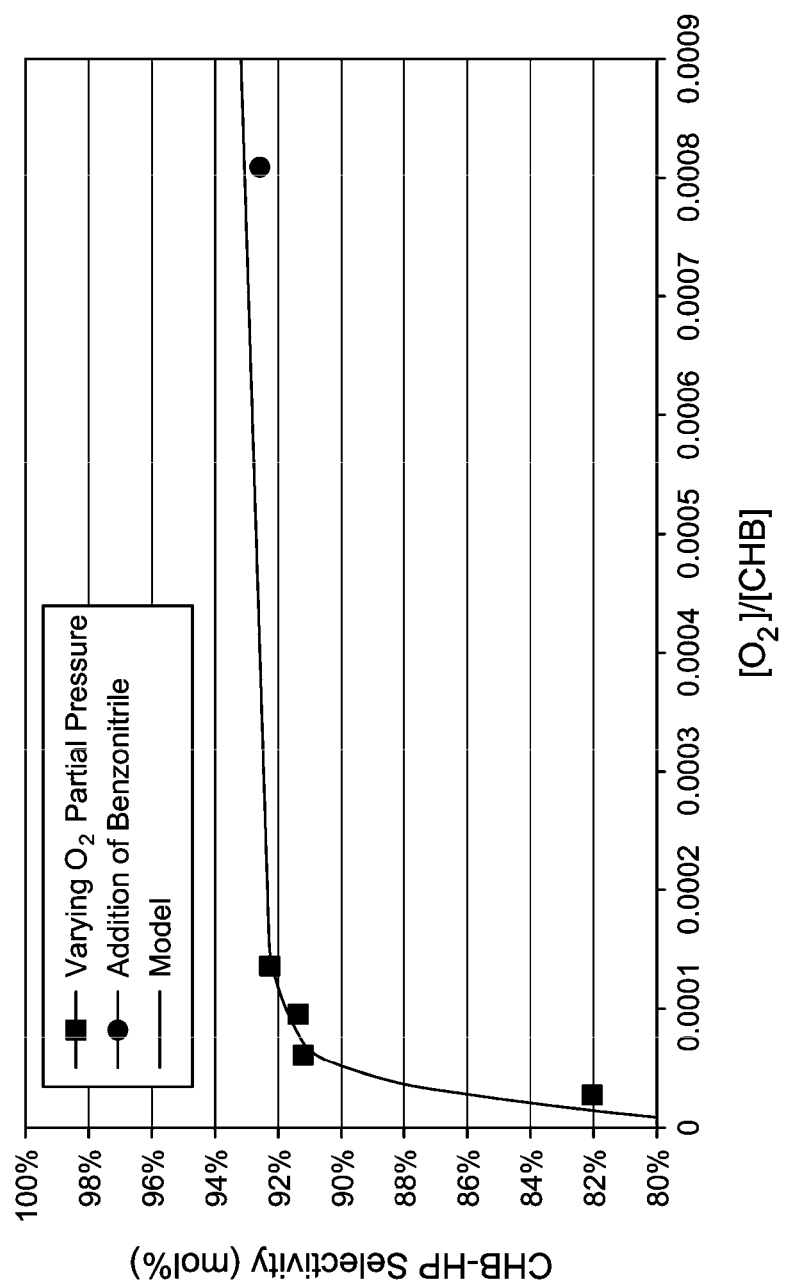
FIG. 3 is a graph of cyclohexylbenzene hydroperoxide selectivity against time on stream at 105° C., 1 atmosphere pressure (100 kPa), and 0.2 wt % NHPI for (a) 100% cyclohexylbenzene and (b) a solution of 20 wt % cyclohexylbenzene in benzonitrile.

Effect of Oxygen Concentration on Oxidation of CHB and 20 wt % CHB/80 wt % Benzonitrile using NHPI as Catalyst The process of Example 1 was repeated with the molar ratio of oxygen:CHB concentration gradually being increased from 0.00001 to about 0.00015. Benzonitrile was then added so as to produce a 20 wt % CHB/80 wt % benzonitrile mixture. The oxygen:CHB concentration was increased to around 0.0008. The actual and predicted effects of these changes on the CHB conversion rate (mol %/hour) and the cyclohexylbenzene hydroperoxide (CHBHP) selectivity are shown in FIGS. 2 and 3, respectively. Thus, it will be seen that the CHB conversion rate increased gradually as the oxygen:CHB concentration increased (FIG. 2), whereas the CHBHP selectivity increased dramatically at first but then plateaued when the oxygen:CHB concentration reached 0.00015 (FIG. 3).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:
1. A process comprising:
(a) providing a mixture comprising cyclohexylbenzene and 10 wt % to 90 wt % of a solvent, the wt % based upon the total weight of the mixture; and
(b) contacting the mixture with oxygen in the presence of a catalyst under conditions effective to produce an oxidation effluent comprising cyclohexylbenzene hydroperoxide and residual solvent, wherein the catalyst comprises a cyclic imide having an imide group of formula (I):

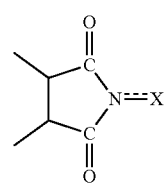

wherein X represents an oxygen atom, a hydroxyl group, or an acyloxy group, and wherein at least a portion of the oxygen is dissolved in the mixture and the liquid phase molar ratio of cyclohexylbenzene to oxygen dissolved in the mixture is less than or equal to 20,000:1.

2. The process of claim 1, wherein the solvent is benzonitrile, acetonitrile, sulfolane, carbon disulfide, nitromethane, nitrobenzene, or a mixture of two or more thereof.

3. The process of claim 1, wherein the solvent is benzonitrile.

4. The process of claim 1, wherein the mixture in (a) comprises from 20 wt % to 80 wt % of the solvent, the wt % based upon the total weight of the mixture.

5. The process of claim 1, wherein the oxygen contacted with the mixture in (b) is diatomic and in a gaseous state.

6. The process of claim 5, wherein the gas is air.

7. The process of claim 1, wherein the liquid phase molar ratio of cyclohexylbenzene to oxygen dissolved in the mixture is less than or equal to 2,000:1.

8. The process of claim 1, wherein the molar ratio of cyclohexylbenzene to cyclic imide contacted with the mixture is less than or equal to 10,000:1.

9. The process of claim 1, wherein the molar ratio of cyclohexylbenzene to cyclic imide contacted with the mixture is less than or equal to 2,000:1.

10. The process of claim 1, wherein said cyclic imide is of the general formula (II):

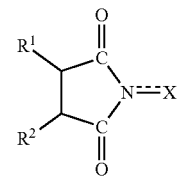

wherein $R^1$ and $R^2$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^1$ and $R^2$ may be bonded together to form a double bond or an aromatic- or non-aromatic ring.

11. The process of claim 1, wherein said cyclic imide is of the general formula (III):

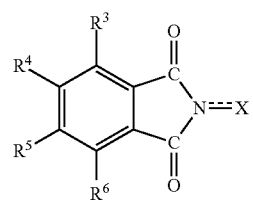

wherein each of $R^3$, $R^4$, $R^5$, and $R^6$ is independently selected from H, aliphatic or aromatic alkoxy radical, carboxyl radical, alkoxy-carbonyl radical or hydrocarbon radical, each of which has 1 to 20 carbon atoms, $SO_3H$, $NH_2$, OH, F, Cl, Br, I, and/or $NO_2$.

12. The process of claim 1, wherein said cyclic imide comprises N-hydroxyphthalimide.

13. The process of claim 1, and further comprising:
(c) contacting at least a portion of the cyclohexylbenzene hydroperoxide produced in (b) with a cleavage catalyst under conditions effective to convert at least a portion of the cyclohexylbenzene hydroperoxide to phenol and cyclohexanone.

14. The process of claim 1, wherein said oxidation conditions comprise a temperature of about 70° C. to about 200° C. and a pressure of about 50 kPa to 10,000 kPa.

15. The process of claim 1, and further comprising:
(d) recovering at least a portion of the residual solvent from the oxidation effluent and recycling at least a portion of the recovered solvent to said providing (a).

16. A process comprising:
(a) contacting benzene with hydrogen in the presence of a hydroalkylation catalyst and under conditions effective to convert at least a portion of the benzene to cyclohexylbenzene;
(b) mixing at least a portion of the cyclohexylbenzene produced in (a) with a solvent to produce a mixture comprising from 10 wt % to 90 wt % of the solvent, the wt % based upon the total weight of the mixture; and
(c) contacting the mixture with an oxygen-containing gas in at least one oxidation zone in the presence of a catalyst and under conditions effective to produce an oxidation effluent comprising cyclohexylbenzene hydroperoxide and residual solvent, wherein the catalyst comprises a cyclic imide having an imide group of formula (I):

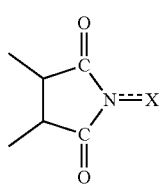

(I)

wherein X represents an oxygen atom, a hydroxyl group, or an acyloxy group, and wherein at least a portion of the oxygen-containing gas is dissolved in the mixture and the liquid phase molar ratio of cyclohexylbenzene to oxygen dissolved in the mixture is less than or equal to 20,000:1.

17. The process of claim 16, wherein the solvent is benzonitrile.

18. The process of claim 16, wherein the liquid phase molar ratio of cyclohexylbenzene to oxygen dissolved in the mixture is less than or equal to 2,000:1.

19. The process of claim 16, wherein the molar ratio of cyclohexylbenzene to cyclic imide contacted with the mixture is less than or equal to 10,000:1.

20. The process of claim 16, wherein the molar ratio of cyclohexylbenzene to cyclic imide contacted with the mixture is less than or equal to 2,000:1.

21. The process of claim 16, wherein said cyclic imide is of the general formula (II):

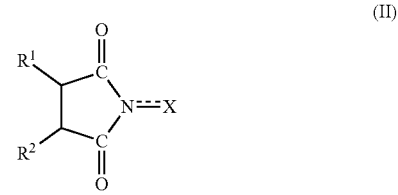

(II)

wherein $R^1$ and $R^2$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^1$ and $R^2$ may be bonded together to form a double bond or an aromatic- or non-aromatic ring.

22. The process of claim 16, wherein said cyclic imide comprises N-hydroxyphthalimide.

23. The process of claim 16, and further comprising:
(d) contacting at least a portion of the cyclohexylbenzene hydroperoxide produced in (b) with a cleavage catalyst under conditions effective to convert at least a portion of the cyclohexylbenzene hydroperoxide to phenol and cyclohexanone.

24. The process of claim 16, wherein said oxidation conditions comprise a temperature of about 70° C. to about 200° C. and a pressure of about 50 kPa to 10,000 kPa.

25. The process of claim 16, and further comprising:
(e) recovering at least a portion of the residual solvent from the oxidation effluent and recycling at least a portion of the recovered solvent to said mixing (b).

* * * * *